(12) United States Patent
Schmitz

(10) Patent No.: US 9,248,055 B2
(45) Date of Patent: Feb. 2, 2016

(54) ON THE FLY SIZE CHANGE APPARATUS AND PROCESS FOR ARTICLES TO BE WORN ON THE LOWER TORSO OF A WEARER AND SUCH ARTICLES

(71) Applicant: CONCEPTS FOR SUCCESS (C4S) E.K., Euskirchen (DE)

(72) Inventor: Christoph Schmitz, Euskirchen (DE)

(73) Assignee: CONCEPTS FOR SUCCESS (C4S) E.K., Euskirchen (DE)

( * ) Notice: Subject to any disclaimer, the term of this patent is extended or adjusted under 35 U.S.C. 154(b) by 26 days.

(21) Appl. No.: 14/348,429

(22) PCT Filed: Sep. 27, 2012

(86) PCT No.: PCT/EP2012/069013
§ 371 (c)(1),
(2) Date: Mar. 28, 2014

(87) PCT Pub. No.: WO2013/045518
PCT Pub. Date: Apr. 4, 2013

(65) Prior Publication Data
US 2014/0288519 A1    Sep. 25, 2014

(30) Foreign Application Priority Data
Sep. 28, 2011    (GB) .................................. 1116718.6

(51) Int. Cl.
*B32B 37/00*    (2006.01)
*A61F 13/15*    (2006.01)
(Continued)

(52) U.S. Cl.
CPC ..... *A61F 13/15699* (2013.01); *A61F 13/15585* (2013.01); *A61F 13/15756* (2013.01); *A61F 13/49* (2013.01); *A61F 13/49058* (2013.01); *B29C 65/08* (2013.01); *A61F 2013/49088* (2013.01)

(58) Field of Classification Search
CPC .................... A61F 13/15699; A61F 13/15585; A61F 13/15756; A61F 13/49; A61F 13/49058; B29C 65/08; B29C 66/81463; B29C 35/0261
USPC .................................. 156/73.1, 580.1, 580.2
See application file for complete search history.

(56) References Cited

U.S. PATENT DOCUMENTS

| | | | |
|---|---|---|---|
| 3,828,367 | A | 8/1974 | Bourgeois |
| 4,940,464 | A | 7/1990 | Van Gompel et al. |

(Continued)

FOREIGN PATENT DOCUMENTS

| | | |
|---|---|---|
| EP | 0641552 | 3/1995 |
| EP | 0974323 | 1/2000 |

(Continued)

OTHER PUBLICATIONS

International Search Report for PCT/EP2012/069013, Completed by the European Patent Office on Nov. 7, 2012, 4 Pages.

*Primary Examiner* — James Sells
(74) *Attorney, Agent, or Firm* — Brooks Kushman P.C.

(57) ABSTRACT

Apparatus and process for the manufacture of articles to be worn on the lower torso of a wearer, such as disposable absorbent article like diapers, training pants, adult incontinence articles, feminine care articles and the like. In particular to such articles and to the equipment and the process for manufacturing such articles, especially when different sizes or types of the article are to be prepared on the same equipment.

3 Claims, 10 Drawing Sheets

(51) Int. Cl.
  *B29C 65/08* (2006.01)
  *A61F 13/49* (2006.01)

(56) References Cited

U.S. PATENT DOCUMENTS

| | | | |
|---|---|---|---|
| 6,059,710 | A | 5/2000 | Rajala et al. |
| 6,312,523 | B1 * | 11/2001 | Caldwell ............ A61F 13/15772 118/123 |
| 7,060,142 | B2 * | 6/2006 | Yamamoto ........ A61F 13/15739 156/290 |
| 7,645,353 | B2 * | 1/2010 | Thomaschefsky ........ B32B 5/26 156/290 |
| 2002/0151422 | A1 | 10/2002 | Duhm et al. |
| 2003/0047273 | A1 | 3/2003 | Kojo et al. |
| 2008/0172020 | A1 * | 7/2008 | Schmitz ............ A61F 13/15747 604/385.06 |

FOREIGN PATENT DOCUMENTS

| | | |
|---|---|---|
| JP | H0856988 | 3/1996 |
| JP | 2004248825 | 9/2004 |
| WO | 2006103487 | 10/2006 |
| WO | 2011064272 | 6/2011 |
| WO | 2011064275 | 6/2011 |
| WO | 2011086054 | 7/2011 |
| WO | 2012042055 | 4/2012 |

* cited by examiner

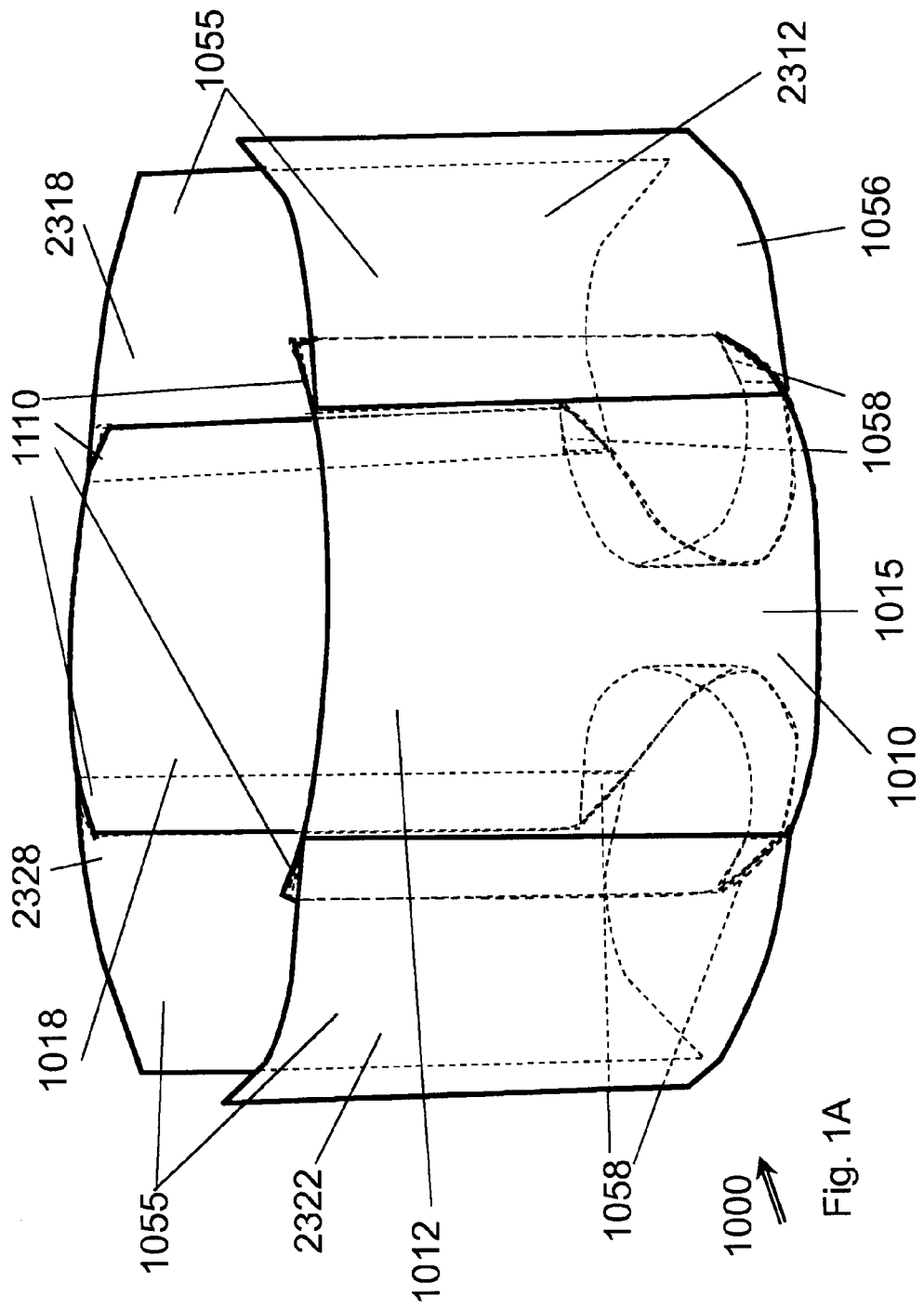

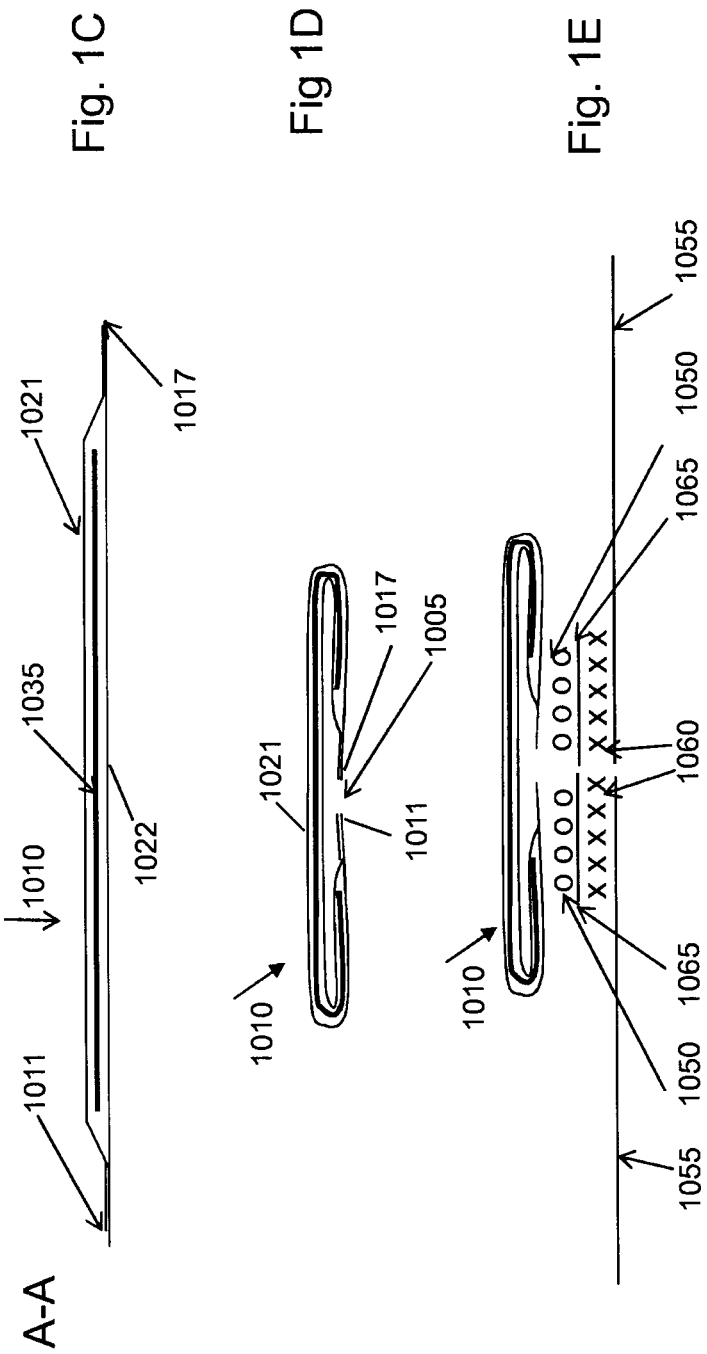

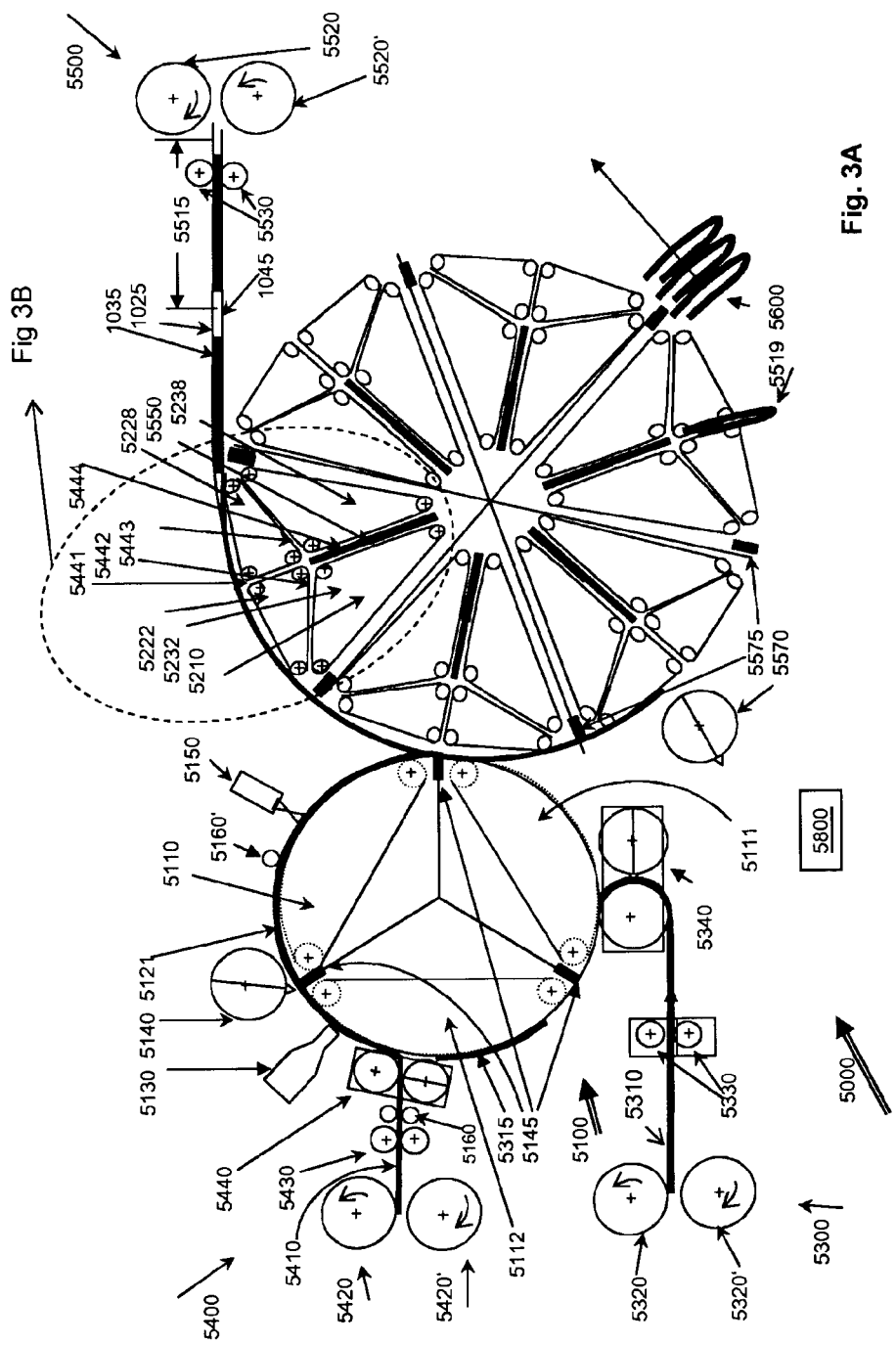

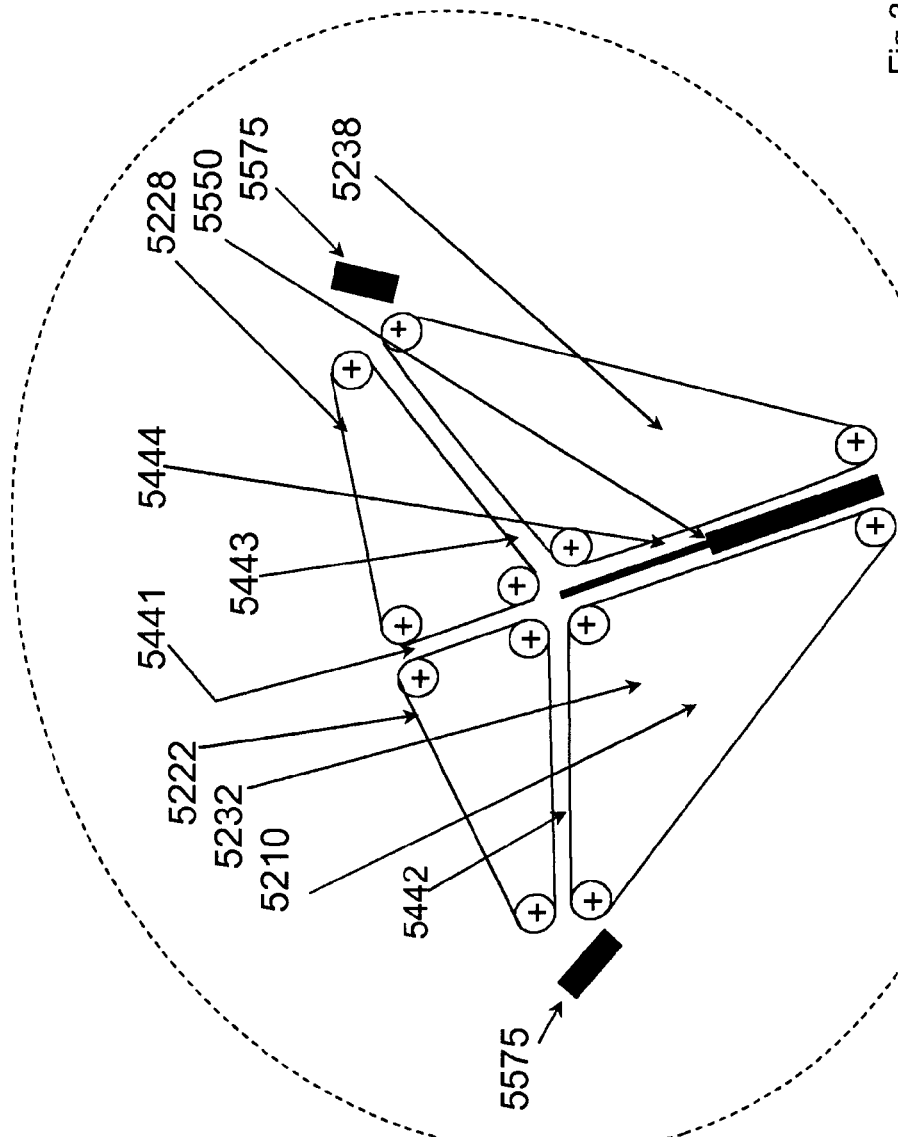

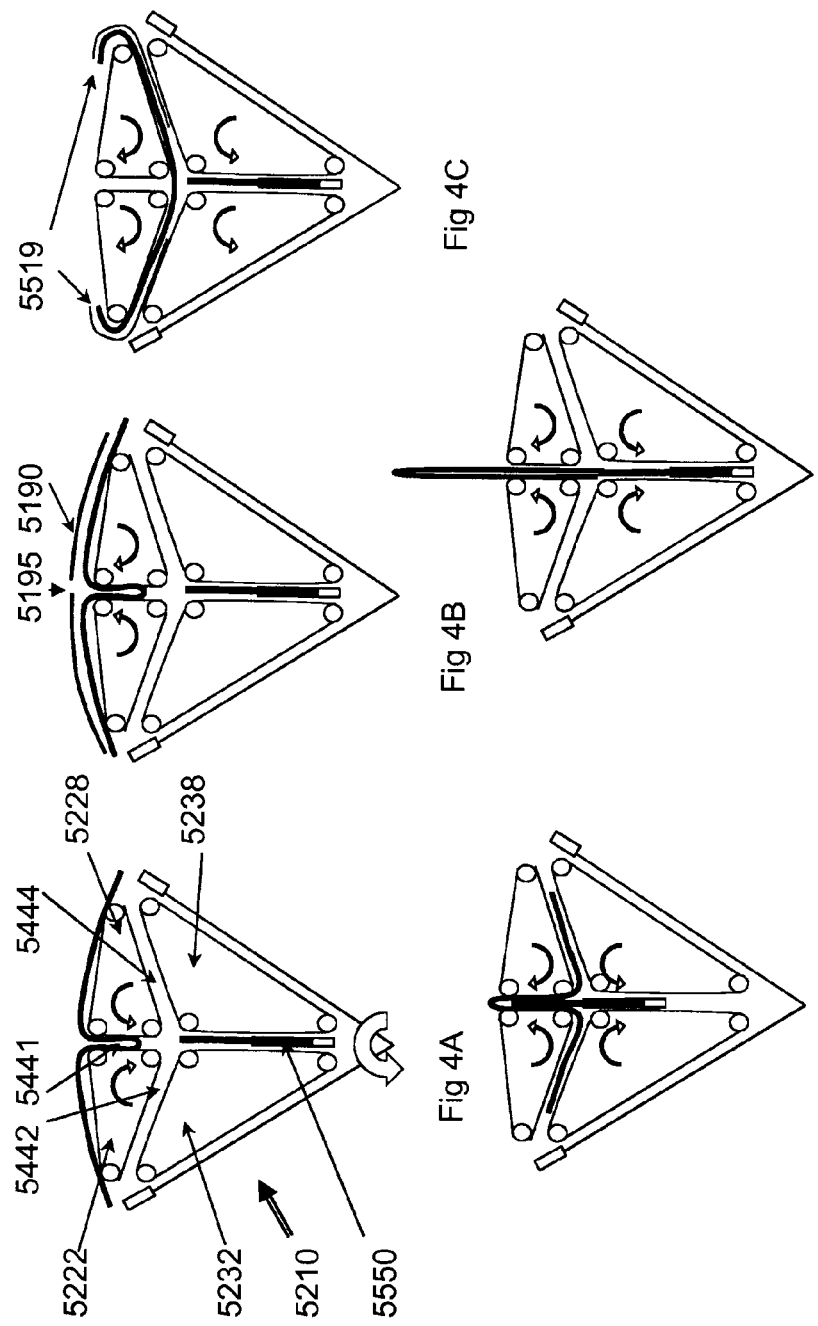

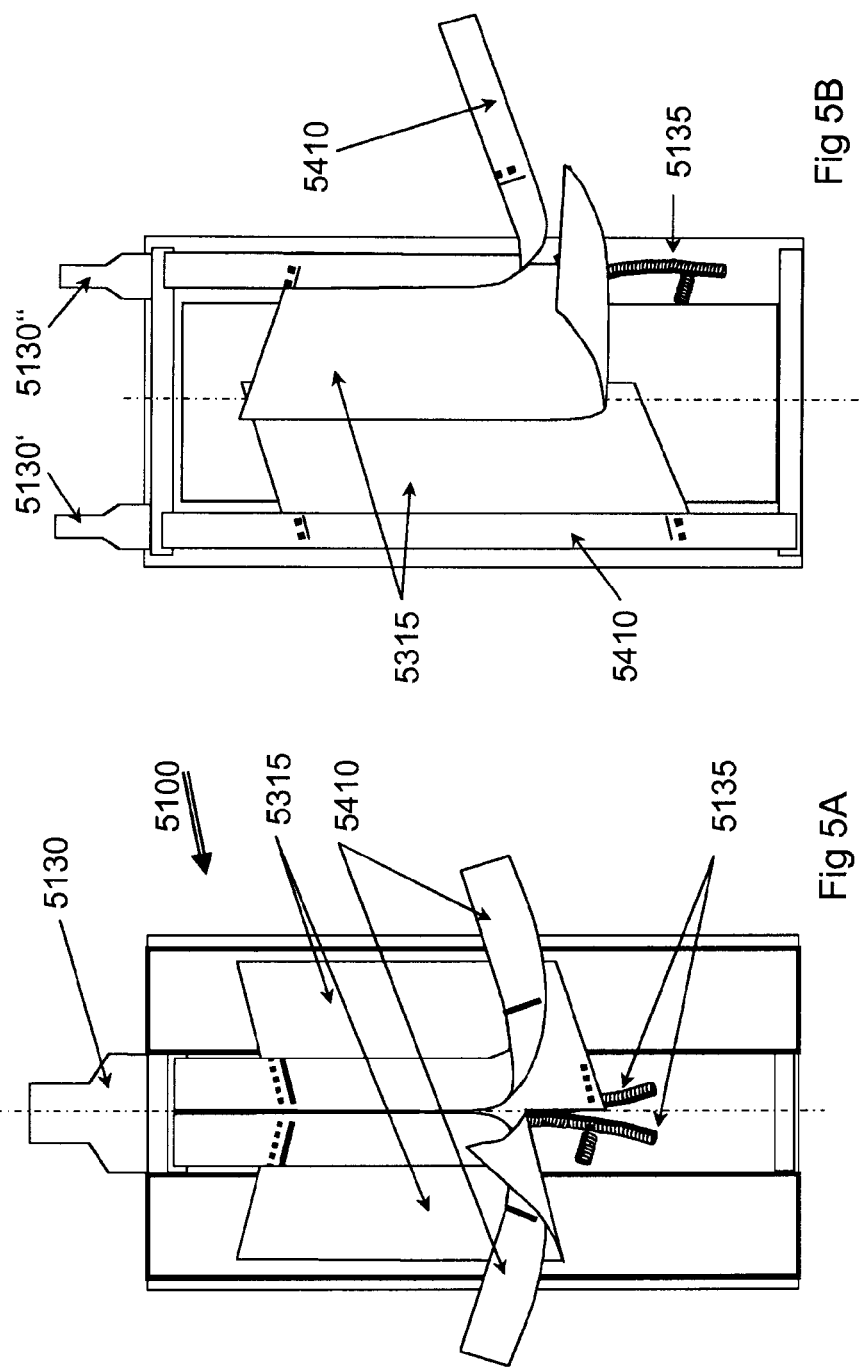

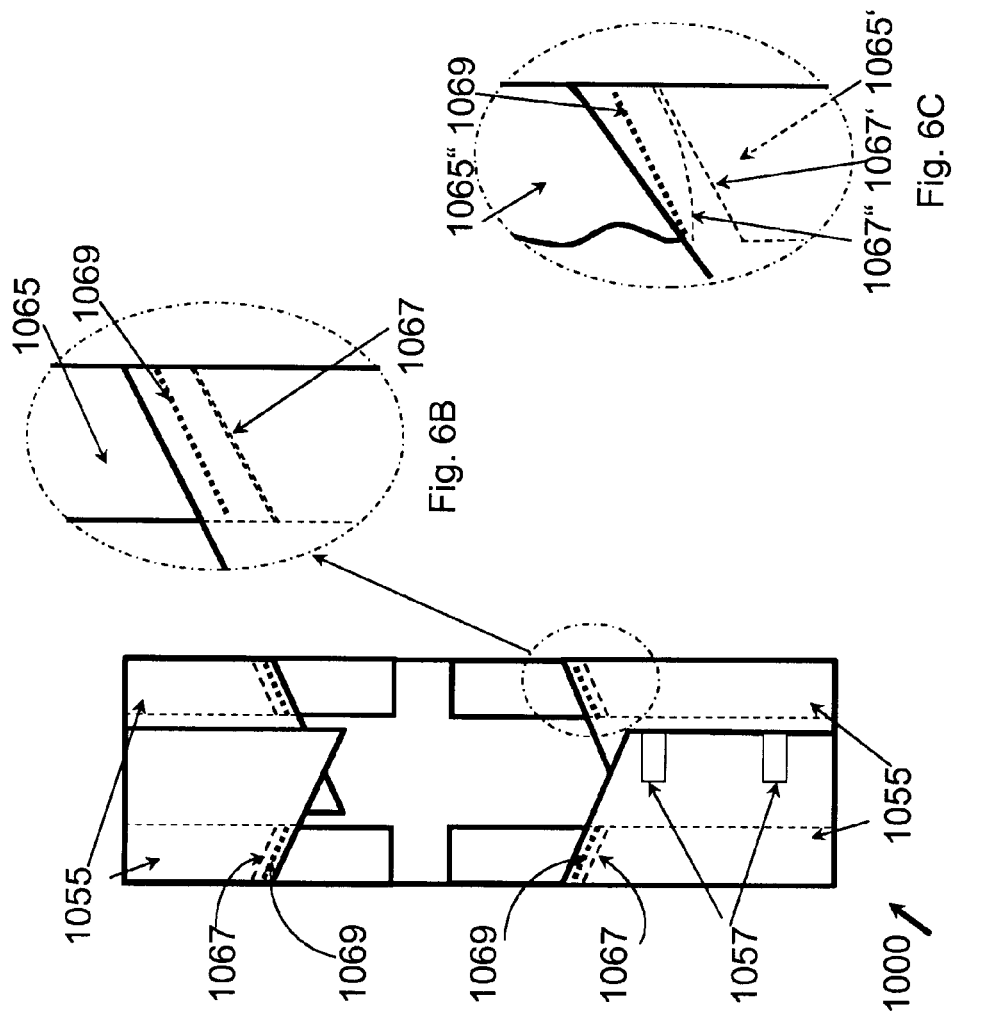

ON THE FLY SIZE CHANGE APPARATUS AND PROCESS FOR ARTICLES TO BE WORN ON THE LOWER TORSO OF A WEARER AND SUCH ARTICLES

CROSS-REFERENCE TO RELATED APPLICATION

This application is the U.S. national phase of PCT Application No. PCT/EP2012/069013 filed on Sep. 27, 2012, which claims priority to GB Patent Application No. 1116718.6 filed on Sep. 28, 2011, the disclosures of which are incorporated in their entirety by reference herein.

FIELD OF THE INVENTION

The present invention relates to the manufacture of articles to be worn on the lower torso of a wearer, such as disposable absorbent article like diapers, training pants, adult incontinence articles, feminine care articles and the like. In particular it relates to such articles and to the equipment and the process for manufacturing such articles, especially if different sizes or types of the article are to be prepared on the same equipment.

BACKGROUND

It is a long lasting desire in the manufacture of articles, and especially of disposable absorbent articles, such as diapers, or at least pre-cursors thereof, to produce various sizes on one and the same manufacturing equipment without tedious, costly, and time consuming change of size specific parts of the equipment.

In JP2004-248825 (Zuiko—Takao) the processing of a sheet in the manufacturing of apparel such as underpant/trouser and diaper is described. The apparels of different sizes are processed in the same apparatus, only by changing the introduction position of the sheets of a constant length.

In US2003/0047273 (Zuiko—Kojo) a semi finished product is manufactured by changing circumferential velocity of the rotating unit, according to the size of semi finished product for each process cycle.

U.S. Pat. No. 3,828,367 (ELASTELLE FONTANILLE—cited in US'273) shows the manufacturing of products such as disposable briefs wherein a flexible non-elastic element on which is fixed locally at least one stretched elastic element adapted to confer on the the non-elastic element the faculty of stretching, the elastic element being fixed in position in the stretched condition. The method comprising essentially the steps of: causing a continuous strip of the non-elastic element to travel, without being subjected to deformation, at a constant speed and always in the same direction; simultaneously causing at least one continuous tape or band of the elastic element to move in the same direction and at the same speed as the strip.

The combining of various webs is a well known operation, such as described in U.S. Pat. No. 6,059,710 (K-C/Rajala), wherein a primary component is cut from a web and is transferred to overlay on a secondary web. The secondary component is then cut on the die to a longer extension, with its longitudinal center coinciding with that of primary component. The combined primary and secondary component are transferred to an embossing roll and engraved with identical shapes. All the die rolls run at different speeds and the center of the components are coincided by adjusting the rotational phase angle of any one of the cutting die rolls.

EP974323A1 (Schmitz) shows a transporting apparatus for manipulating a continuous web which has support surfaces lying in an arc around the circumference of a circular path, which with web loop forming means give variable velocity difference between the adjacent web supports, are rotated about the axis of the circular path, such that distances between adjacent supporting surfaces vary upon rotation. EP1004285A1 (Schmitz) discloses a web handling process, wherein a web portion moves quicker when a portion is cut into separate lengths, than when it is cut off the web. The web portions are applied to a receiving web, which is then cut.

In WO2006103487A1 (Schmitz, C4S) the described method involves a moving web material from a web supply unit towards a process end section along an overall web path. A web path splitting unit positioned along the overall web path is provided. The web path is divided on the web path splitting unit into web sub-paths. The web material is transferred out of initial contact regions of a web support unit into an operating region of the web support unit. The web material is transferred out of the initial contact regions of web support unit into the operating region, thus precisely handling the web material in an efficient manner.

However, in none of the cited documents there is taught a way how to allow manufacturing articles of varying sizes over a very wide size range essentially uninterruptedly ("on the fly") at high speeds, nor how to design a respective equipment. Also, nowhere is taught how to make both a closed pant structure in the same machine as an open type diaper without changing significant parts of the manufacturing line.

SUMMARY

Thus, in a first aspect, the present invention is a method for the manufacture of an article, which comprises segments of a centre piece web material, separated pieces of a side panel web material, and pieces of a leg hoop web material connected to the side panel web pieces. The method comprises the following steps:

providing a first essentially continuous web for forming the centre piece at a predetermined variable first web supply speed;

providing a second essentially continuous web material for forming the leg hoop materials at a predetermined variable second web supply speed;

providing a third essentially continuous web material for forming side panels at a predetermined variable third web supply speed;

providing a first turret for combining the second and third web materials, the turret being mounted for rotating at a predetermined variable first turret speed and comprising at least two web support means, each comprising a web support means surface which can be moveable at a predetermined variable web support means surface speed, relative to the turret surface speed and being adapted for temporarily attaching the first and second web material or segments thereof thereon;

a side panel separating means for separating pieces at a predetermined variable cut length from the third web;

a side panel/leg hoop composite separating means for separating pieces of the side panel/leg hoop composite at a predetermined cut length;

providing a second turret for combining the side panel/leg hoop composite with the centre piece web, preferably positioned in a "kissing relation" to the first turret and comprising:

at least two web handling sections, each web handling section comprising at least two, preferably three, more preferably four web handlings means each comprising a web support means surface which is moveable at a predetermined variable web support means surface speed, relative to the turret surface speed,
a centre piece separation means;
an article discharge means;
providing a controlling unit for adjusting respective speeds and positioning of web support means, connecting means, applications means or the pusher means;
feeding the side panel web towards the side panel separating means at a first web speed and separating a side panel piece from the side panel web at a side panel cut length;
positioning the side panel piece on one of the first turret web support means, thereby spacing subsequent side panel pieces apart by adjustment of first turret web support means surface speed;
feeding the leg hoop web to the web support means of the first turret at a predetermined variable speed such that it overlays the side panel piece;
connecting the side panel piece and the leg hoop web, preferably by ultrasonic welding to form the side panel/leg hoop composite;
separating subsequent pieces of the side panel and leg hoop material in the spacing between two subsequent side panel cut pieces at a predetermined/variable leg hoop material cut length;
feeding the centre piece web at a predetermined variable speed to the second turret;
applying combining adhesive onto the surface of the side panel/leg hoop composite or to the centre piece;
adjusting the surface speed of the two outer web support means of the second turret such that a predetermined portion in the crotch region of the centre piece web is dislocated radially inwardly into the first gap between two web support means;
rotating the first and the second turret at a matched surface speed such that the combined side panel/leg hoop composite pieces are positioned in registry with the portions of the centre piece web, which are not dislocated radially;
separating pieces of the centre piece web, optionally after the combination with the side panel/leg hoop composite to form individual articles;
transferring the article out of the turret.

In addition to these essential steps, the method may further optionally comprise one or more of the steps of
applying a curved connection when combining the side panel web and the leg hoop web;
applying ultrasonic energy, preferably working against a flexible anvil for connecting;
further treating the individual article in the treatment section or on the turret;
connecting permanently front and rear portions of the article at the unconnected longitudinal side margins of the side panels to form a closed pants-style article;
applying closure means to the front or rear portion of the article;
connecting the front and rear portions of the article by means of these closure means so as to form re-openable pants-style articles;
maintaining the treatment sections and web handling means on the turret in a fixed position relative to each other;
overfolding the longitudinal side margins of the centre piece web prior to or during feeding the centre piece web to the first turret;
applying predominantly cross-directionally extending connecting lines to the side panel pieces and the leg hoop material whilst the first longitudinally extending side margins of the overlaid side panel and leg hoop webs are extended compared to the second opposite longitudinally extending side margin of the leg hoop web, which is the one which is closest to the crotch crease on the product in use.

The method is particularly useful allowing an "on-the-fly" change in the manufacture of at least two sizes or types of article series. The articles comprise segments of a centre piece web, which exhibit different dimensions for different sizes at least for the length of the article corresponding to the machine direction of the manufacturing method, separated pieces of a side panel web, which exhibit different dimensions for different sizes at least for the length of the article corresponding to the machine direction of the manufacturing method, and pieces of a leg hoop web material, which exhibit essentially the same dimension for the varying sizes. The method comprising the at least the essential step and may comprise one or more of the optional steps as described in the above and further comprises the steps of
selecting one or more characteristic design parameter for the article sizes or types,
adjusting the variables of the process steps according to claim 1 or claim 2 according to a preset correlation as being stored or calculated in a programming and control unit.

In another aspect, the present invention is an apparatus for the manufacture of differently sized articles to be worn on the lower torso of a wearer. The articles comprise segments of a centre piece web, which exhibit different dimensions for different sizes at least for the length of the article corresponding to the machine direction of the manufacturing method, separated pieces of a side panel web, which exhibit different dimensions for different sizes at least for the length of the article corresponding to the machine direction of the manufacturing method, and completely or partially separated pieces of a leg hoop web, which exhibit essentially the same dimension for the varying sizes.

The apparatus comprises:
a first, a second, and a third web supply means for delivering a centre piece web, a leg hoop web, and a side panel web, respectively;
a first turret, comprising at least two first turret sections, each comprising a web support means, and being adapted for rotating at a first turret speed;
a second turret adapted for rotating at a second turret speed and comprising at least two second turret sections, each comprising web support means for handling segments of the centre piece, and a foreshortening means for adjusting the distance of the leading and trailing edges of the segments of the centre piece and for dislocating the foreshortened portion of the segment away from the surface of the turret;
separation means for separating subsequent pieces of the centre piece, of the leg hoops and of the side panels, and for applying optionally discontinuous separation lines to the leg hoop web;
a first connecting means, preferably an ultra sonic welding means, for connecting the leg hoop web to the side panel pieces and a second connecting means, preferably a glue application means, for connecting the centre piece to the combined leg hoop and side panel composite;
a programming unit for controlling and adjusting
the supply web speeds;
the first turret rotating speed,
the second turret rotating speed;
the web support speed of the web supports of the turrets;
the connecting means and the separating means;

at any predetermined ratio relative to the preset length of the separated pieces of the leg hoop web.

The apparatus may further comprise a pusher means positioned radially moveable between two web handling means of the second turret adapted for supporting the dislocation of the separated pieces of web material. Preferably, the first connecting means is an ultrasonic welding means with a flexible size adjustment capability.

In yet a further aspect, the present invention is an article for being worn on the lower torso of a wearer, which comprises segments of a centre piece web material, separated pieces of a side panel web material, and pieces of a leg hoop web material connected to the side panel web pieces, preferably by a curved connection line. The leg hoop web material and the side panel web material form a leg hoop/side panel composite which is connected to the segments of the centre piece web such that the side panel web material is connected to the centre piece segments essentially only via the leg hoop material. The leg encircling hoop during use is formed by portions of the centre piece, the side panel pieces and the leg hoop material pieces. Optionally the leg hoop piece is connected to the side panel piece and on an opposite surface to the centre piece.

In a further aspect, the present invention is a size line-up consisting of at least two of such articles differing in size or connection type of the side front and rear side panels. In a preferred execution, the pieces of leg hoop material exhibit for different sizes essentially the same length dimensions.

BRIEF DESCRIPTION OF THE FIGURES

FIG. 1A to C show schematic views of an article according to the present invention.

FIGS. 3 A and B show a schematic outline of the equipment according to one aspect of the present invention on which a process according to another aspect of the present invention may be executed to produce an article according to a further aspect of the present invention.

FIG. 4 A to E depict schematically the process steps during the making of an article in the section of production turret with four web support means interacting.

FIGS. 5 A and B depict schematically two options for positioning materials on a first combining unit.

FIG. 6 A to C show schematically details of a further variant of an article according to the present invention.

Same numerals depict same features. Dimensions are not necessarily to scale.

DETAILED DESCRIPTION

The present invention is directed towards the manufacture of articles to be worn on the lower torso of a wearer, such as pants or pants-style products, which have a pants shape by exhibiting a closed waist hoop and wherein the front and rear portions are connected to each other in the side or hip regions, but also to diapers, on which the front and rear portions are not permanently connected, but are either unconnected as in the case of open-style diapers, which are brought into a pants-style fit by the user or a caretaker, or are pre-closed, such as when recloseable closure means are closed during manufacturing, which the user or care taker can non-destructively open for removal, re-use or for fit adjustment. The article may exhibit a liquid absorbency capability such as for disposable absorbent articles like diapers. Alternatively, the articles may exhibit no or only a very limited liquid absorbency, such as may be useful for disposable or washable and re-usable underwear, or for fixation pants as may be used in so called two-piece systems comprising a pad with liquid absorbency and fixation pants, which may also be in the pre-closed diaper style.

The following explanation is done in the context of the manufacturing of a disposable absorbent article, such as a baby or adult incontinence diapers, which may also be produced in a pre-closed state or as a pant-style diaper. However, the skilled person will readily realize how to apply the teaching also to other articles. Within the context of the present description, the term "article" shall also comprise "pre-cursor of an article", such as when an unfinished precursor, which is made according to the process described herein is finished such as by adding further elements or features.

The present invention is based on the principle that a product, and in particular a three-dimensionally shaped one—when in an in-use configuration—can be obtained by the combination of at least three essentially flat web materials. A first and a second of these web materials are combined such that pieces of a first material are positioned on and connected to the second one in a longitudinal spaced apart relation (relative to the longitudinal direction of the article and to the machine direction of the process). This composite is further combined with the front and rear parts of a third material, whilst at least portion of the third material is folded away, i.e. the third material is foreshortened so as to match the length of the composite.

This principle is now further explained in more detail for the respective product, an equipment suitable for manufacturing such a product, and a respective manufacturing process.

Figure 1B:
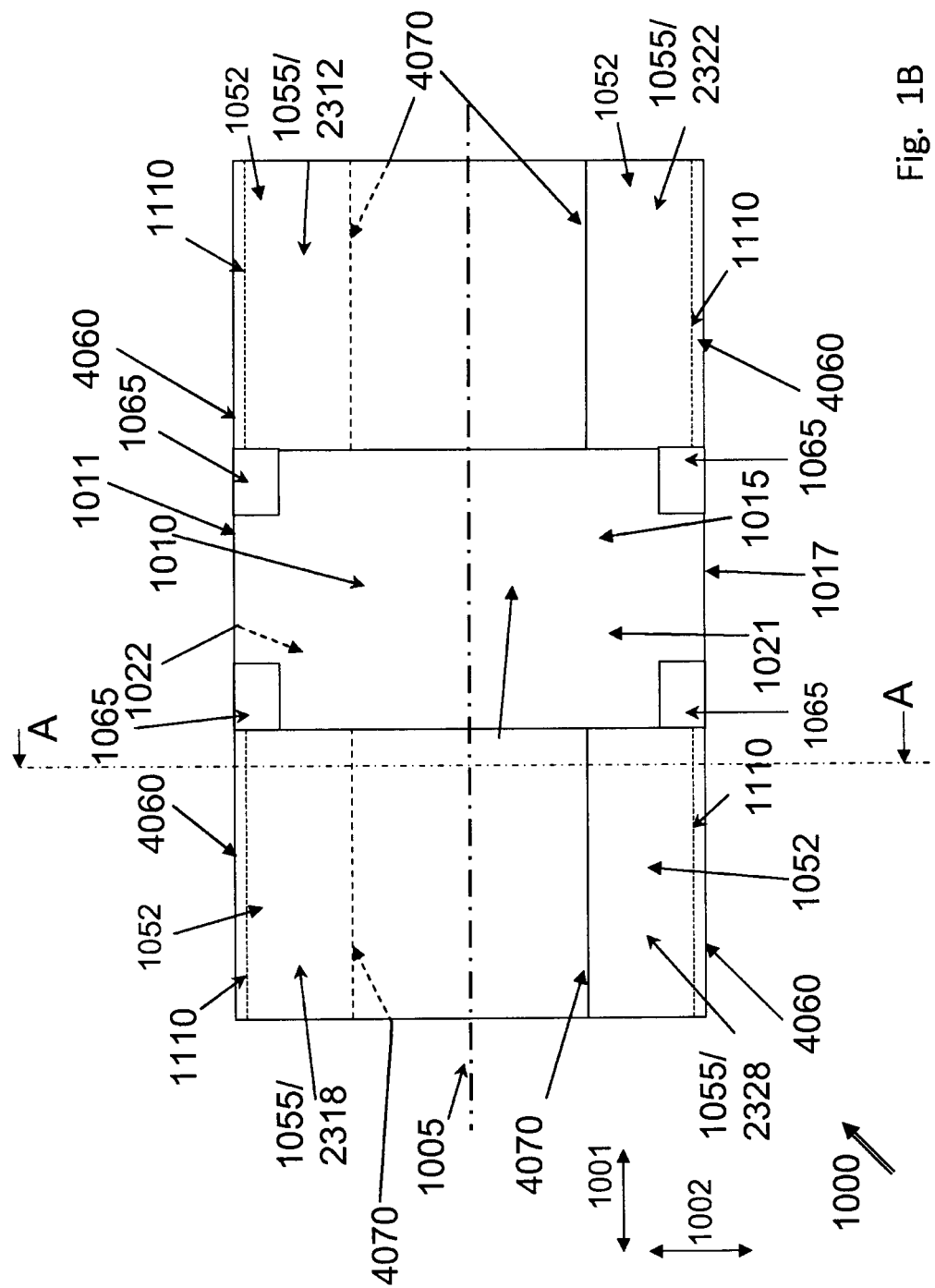

Thus referring to FIG. 1, such an article is schematically depicted, with FIG. 1A showing a perspective view of such an article in a ready-to use configuration, and FIG. 1B showing the article in a pre-use configuration, e.g. during manufacturing or in a packaging. A general feature of such an article is that it is combined from essentially flat, and often non-elastic material, yet providing a three-dimensional structure adapting to the body contours of a wearer. The article comprises leg hoops encircling the upper thigh of a wearer during use. Within the present context, the leg region of a standing wearer extends from the crotch line downwards, whereby the crotch line is defined by the crotch crease or groin adjacent to the pubic area and an essentially horizontal circumferential line through the groin laterally outwardly around the leg.

The article 1000 comprises a front (1012) and a rear region (1018), typically corresponding to the waist regions of a wearer, and a crotch region (1015) there between, thereby defining the longitudinal (x-) orientation (1001) of the article. A width direction (1002) extends perpendicular thereto, as well as the thickness or z-direction. A centre piece 1010 extends from the front through the crotch to the rear region exhibiting a first (1011) and a second longitudinally extending side margin (1017).

The article exhibits in its ready-to-use or in-use configuration a surface which is generally oriented towards the wearer, which is often referred to as inner or topsheet surface. An opposite surface is generally oriented away from the wearer and often referred to as outer or backsheet surface. Within the present context, first surface (1021) of the centre piece corresponds to the outer surface of the centre piece, whilst the opposite surface (1022) corresponds to the inner surface of the article. The term "generally oriented" includes that certain portions of the surface may be folded such that they face towards a different direction, Such articles fit relatively tight to the body, such that the rise on a wearer (i.e. the length from the back waist margin of the article through the crotch of a wearer to front waist margin of the article) corresponds almost to the overall length of the article.

The article further comprises side panel regions 1055, which extend laterally outwardly of the centre piece 1010 when the article is in its in-use configuration. In a pre-use configuration, the side panels 1055 may be positioned so as to overlay the centre piece 1010. The article further comprises a first and a second leg hoop materials positioned between the side panels and the centre piece, which during use encircle the left and right upper thighs of a wearer.

The article comprises at least a first (2318) and a second rear (2328), and preferably a first (2312) and a second front (2322) side panel wherein each of the side panels exhibit a first and second longitudinally extending side margin connected to the leg hoop material and via this to the centre piece in connecting regions, respectively. The connecting regions of the centre piece extend essentially along the side margins of the centre piece in the rear region and optionally front region of the centre piece and the side panel connecting regions extend essentially along the first side margins of the side panels.

The side panels exhibit a first surface, oriented towards the wearer during use, and a second surface, oriented away from the wearer during use. The surfaces may have different properties, but often the side panels are made from a homogeneous or symmetrically build up material, such that the differences of properties are inexistent, marginal or irrelevant. At least in the pre-use configuration as shown in FIG. 1B, the centre piece and the side panels may be positioned such that their second surfaces are oriented towards each other, e.g. the viewer sees in FIG. 1B the backsheet surface 1021 of the centre piece and the wearer oriented (inner) surface 1052 of the side panels. As shown in this particular execution, the first front (2312) and rear (2318) side panels are positioned overlappingly relative to the second front (2322) and rear (2328) side panels.

The first side margins 4060 of the side panels are positioned to overlay the first side margins 1011 and 1017, respectively, of the centre piece. Through this arrangement, the second side margins 4070 of the first and second rear and optionally front side panels extend towards and optionally beyond the longitudinally extending centre line of the centre piece, but not into the connecting region of the respective opposite side panel.

The side panels are shown as individual web pieces connected via the leg hoop material to the centre piece in the connection regions 1110, here shown as straight lines, but preferably executed as curved lines. It should be noted that within the context of the present invention a connecting line might be exchangeably used with a connecting region, which may be circumscribed by straight or curvilinear boundaries. Also, a line or a region may be executed in an interrupted pattern, such as a dotted line, or a region with a hash pattern A curved connecting line provides a particular effect, as described in more detail in co-pending application WO2011/064275, to which express reference is made for this "darting effect". The connecting may be achieved by any conventional means, in a preferred execution it is an ultrasonic or heat pressure bond. These connection regions extend essentially along the first (1011) and the opposite second (1017) longitudinally extending side margins of the centre piece 1010 at least in the rear region and—as shown in FIG. 1B—also in the front regions and the corresponding connecting regions of the side panels along a first longitudinally extending side margin of the side panels. Considering the first rear side panel 2318, the second longitudinally extending side margin 4070 is positioned away from the first longitudinally extending side margin 1011 of the centre piece towards the longitudinally extending centre line 1005 or beyond, but not into, the connecting region of the second rear side panel.

It should be noted, that in the in-use configuration, the leg of the wearer is encircled by a portion of the centre piece 1015, a portion of the side panel 1055, and a portion of the leg hoop material 1065.

Optionally, the side panels may be folded or even be multiply folded, such as in an "accordion" or "leporello" type of fold. Optionally, the sidepanels are composed of more than one web, connected to each other along connecting lines or regions in a butt-type or an overlapping connection.

FIG. 1C to 1E depict a a cross-sectional views of an unfolded centre piece (FIG. 1C), a longitudinally folded centre piece (FIG. 1D) and a composite of the folded centre piece with the side panels 1055 and the leg hoop material 1065 there between (FIG. 1E). The longitudinal side margins 1011 and 1017 of the centre piece 1010 are overfolded towards the centre line 1005 of the article such that the first (or wearer oriented) surfaces 1022 are oriented towards each other. In the crotch region, this overfold may be stabilized by connecting the surfaces to each other, such as by conventional glue bonding. Side panels 1055 may be connected to the centre piece 1010 via leg hoop material 1065, with connections 1060 between the side panels 1055 and the leg hoop material 1065 indicated as "xx", and the connection 1050 between the leg hoop material 1065 and the centre piece 1010 as "oo".

A particularly preferred execution of an article comprises a "faeces trap" as described in more detail in WO2011/0644272. Therein, the topsheet is longitudinally slit and comprises further preferably longitudinally extending elastics positioned adjacently to the longitudinal slit.

It should be noted that the present description applies to a finished article as well as to a pre-cursor as can be readily converted into a finished article, such as by adding further features, such as closure tapes or by connecting the first front and rear and second front and rear side panels so as to form a pants style article. The article may be in a "ready to use" or "in use" configuration as shown in FIG. 1A or in a "pre-use" configuration as for example shown in FIG. 1B.

Generally, the term "web" relates to any material which is essentially endless or continuous in one direction (generally denoted as "x-direction" or "machine direction"). Webs are often, but not necessarily, stored, supplied or used in roll form and thusly also sometimes denoted "roll goods". Whilst these are then not "endless" in the strict sense of the word, their extension in this x-direction is significantly larger than in any other direction. By combining consecutive rolls or other batches, ("splicing") such webs can be considered "endless" for all practical purposes. Webs may be transported in a "batch" form, such as when a roll thereof is shipped, or they may follow a "web path", such as when the webs are unwound from a roll, as described hereinafter.

Often, but not necessarily, webs have an essentially uniform thickness (herein denoted as "z-direction", and also constant width (herein denoted as "y-direction") along the x-directional length. Webs may be of essentially uniform composition, they can be mixtures of materials, they can be composites of materials such as being layered (different materials arranged in a juxtaposed position in the z-direction) and/or can comprise stripes of different materials or materials having different or varying properties (i.e. arranged in a juxtaposed position in the y-direction).

Typical examples for webs are—without implying any limitation—flexible, e.g., plastic films or foils, textiles, nonwovens, nets, scrims, paper, or cartons.

The centre piece material is a web material made of at least one layer of material with suitable properties with regard to its intended use, i.e. allowing to be worn as an article, and with regard to be useful in the context of the present invention, i.e. allowing to be connected to other material. In case of the article being a disposable absorbent article, the centre piece typically comprises materials exhibiting a liquid absorbency, enveloped between other web materials, one of which may be liquid impermeable and function as a backsheet, and the other one may be liquid permeable and function as a topsheet, which are all well known in the art.

The selection of the liquid absorbent material is not critical within the present context, it may be a distinctly formed material, such as known absorbent cores, or may be a web material, such as airlaid webs.

The enveloping can be achieved by conventional means, such as gluing, thermo-bonding, ultrasonic bonding etc.

In addition to or integral with the absorbent core or the enveloping material, further materials may be added. For example, if the absorbent core comprises particulate material such as superabsorbent material, particle restraining means, such as paper tissues or nonwoven webs with an adapted pore size, may be added. Also, further liquid handling means may be added, such as "acquisition-distribution-layers".

A backsheet material may be a liquid impervious backsheet, as known in the art. It may include the first material described herein. An example backsheet herein includes a laminate sheet of a nonwoven layer and a film layer or a film-coated nonwoven layer, whereby in either case the backsheet or the nonwoven layer may be, or may include, the first material described herein. Hereby, the film layer or film coating faces the absorbent core of the article; the nonwoven layer may form part of the external surface of the article, and may thus for example face the wearer's cloths in use. The backsheet may include a nonwoven layer on its external surface, or the backsheet may include a laminate layer of a film and a nonwoven, or a film-coated nonwoven layer.

The topsheet may be compliant, soft feeling, and non-irritating to the wearer's skin. The topsheet should be liquid pervious permitting liquids (e.g., urine) to readily penetrate through its thickness at least in certain regions thereof. The topsheet may include or essentially consist of a nonwoven material and/or an aperture film material. In a particular execution, the centre piece may be designed for separating faeces from the skin of a wearer, such as described in more detail in co-pending application WO11/064272.

According to the present invention, the backsheet as part of the centre piece is connected to the side panels via the leg hoop material. As the latter may strengthen the connection between the centre piece and the side panels, the backsheet material may exhibit a lower material strength than in conventional designs. It is important that the leg hoops are at least as long as the side panels connected to them when measured along the leg hoop to side panel connecting lines.

Also the side panels can be made from one or more web materials. Preferably, the side panel material is air permeable so as to prevent occlusion of the skin of the wearer. The side panel material may be a nonwoven material, comprising thermoplastics, such as polypropylene, polyethylene, and the like. The side panel material may be essentially inelastic, such as when made as a nonwoven web from conventional polyolefins, it may be elastic, either uni-directionally, such as when e.g. parallel elastic threads are included, or bi- or multidirectional, such as when e.g. elastomeric film- or fibre-based materials are used in nonwovens.

Also the leg hoops are made from web materials, which may be of the same type as the side panels, except that preferably, the leg hoop web is inelastic in its machine direction. It is a particular benefit of the present invention that articles of different types and sizes can be manufactured on one and the same manufacturing equipment without exchanging parts of the machine or even without stopping the machine ("on-the-fly"). Thus, within the present context, the term "size line up" refers to a set of articles, which have some common characteristics as known from a product range of one product type, e.g. a set of baby diapers of one supplier covering various sizes, but which can be manufactured on one manufacturing unit. In the present context, this is enabled by positioning the leg hoop material between the side panel material and the centre piece, allowing to use different sidepanel to leg hoop bond geometries for different sidepanel lengths on different size products, such that the product size can be varied across an extremely broad range. It should be noted, that also a change between e.g. closed type products, such as pants, and open type products, such as open type diapers, or pre-closed products can be done "on the fly".

In a particularly preferred execution all products of the size line up exhibit a constant leg hoop material length and the size changes are adjusted "on-the-fly" by adjusting cut lengths of the other materials. This is explained in more detail when referring to FIG. 2A, which schematically shows an article 1000 according to one particular execution of the present invention with important dimensions. For ease of presentation, the three-dimensional effect of the curved connecting line between the leg hoops, to which the centre piece is connected, and the side panels, resulting in the above mentioned "darting effect" is only cursorily depicted.

The article as shown is in its "ready to use configuration" after the side panels have been folded outwardly. If the article is a closed pants structure, such as training pants or the like, the following discussion applies to a "opened pants configuration", i.e. when the connections of the front to the rear portions have either been not yet made or re-opened, and the article is laid out.

The article exhibits an overall length 1501 and an overall width 1502. The article as shown has four side panels, a first front 2312, a second front 2322, a first rear 2318 and a second rear 2328, whereby "first" and "second" may denote "right" and "left", respectively. They are shown as matching trapezes, such that the front and rear panel may be cut from a single piece or web. Thus, the front panels have a shorter edge length 1521 where they are connected to the centre piece and a longer edge length 1523 at their free side margins. Accordingly, the rear panels have a longer edge length 1529, where they are connected via the leg hoop materials to the centre piece and a shorter edge length 1527 at their free edge. The side panels exhibit a side panel width 1518 and 1528 respectively, which here refers to the width they extend laterally outwardly of the centre piece (i.e. the overlap region, where they are connected to the leg hoops, preferably by a curved connecting line, is not considered here).

The article as shown has further leg hoop portions, namely a first front portion 1312, a second front portion 1322, a first rear portion 1318 and a second rear portion 1328. The front and the rear portions and most preferably also the first and second portions all exhibit the same leg hoop material width 1610. The front portions exhibit a front leg hoop length 1623, and the rear leg hoop portions exhibit a rear leg hoop length 1629. The front and the rear leg hoop portions are longitudinally spaced apart by the leg hoop gap 1601. It should be noted, that when the article is put into a "ready to use" or "in-use" configuration, the waist circumference is primarily influenced by the centre piece width and the side panel width, and the leg circumference primarily by the length of the free leg hoop material portions 1624 and 1628 and the leg hoop gap 1601, in addition to the side panel width upon adjustment of the overlap of front and rear side panels. The term "free leg hoop material portion" relates to the portion of the leg hoop material which is not overlaid by the side panels, respectively which extends from the separation lines 1067 towards the crotch region of the article.

FIG. 2B to G depict schematically how to simply accomplish variations of certain dimensions which allows a wide adjustment of product sizes by maintaining the leg hoop length constant across all sizes. These product executions relate to a particularly preferred production method, wherein all sizes of a size line up have essentially same length leg hoop materials.

Figure 2A:
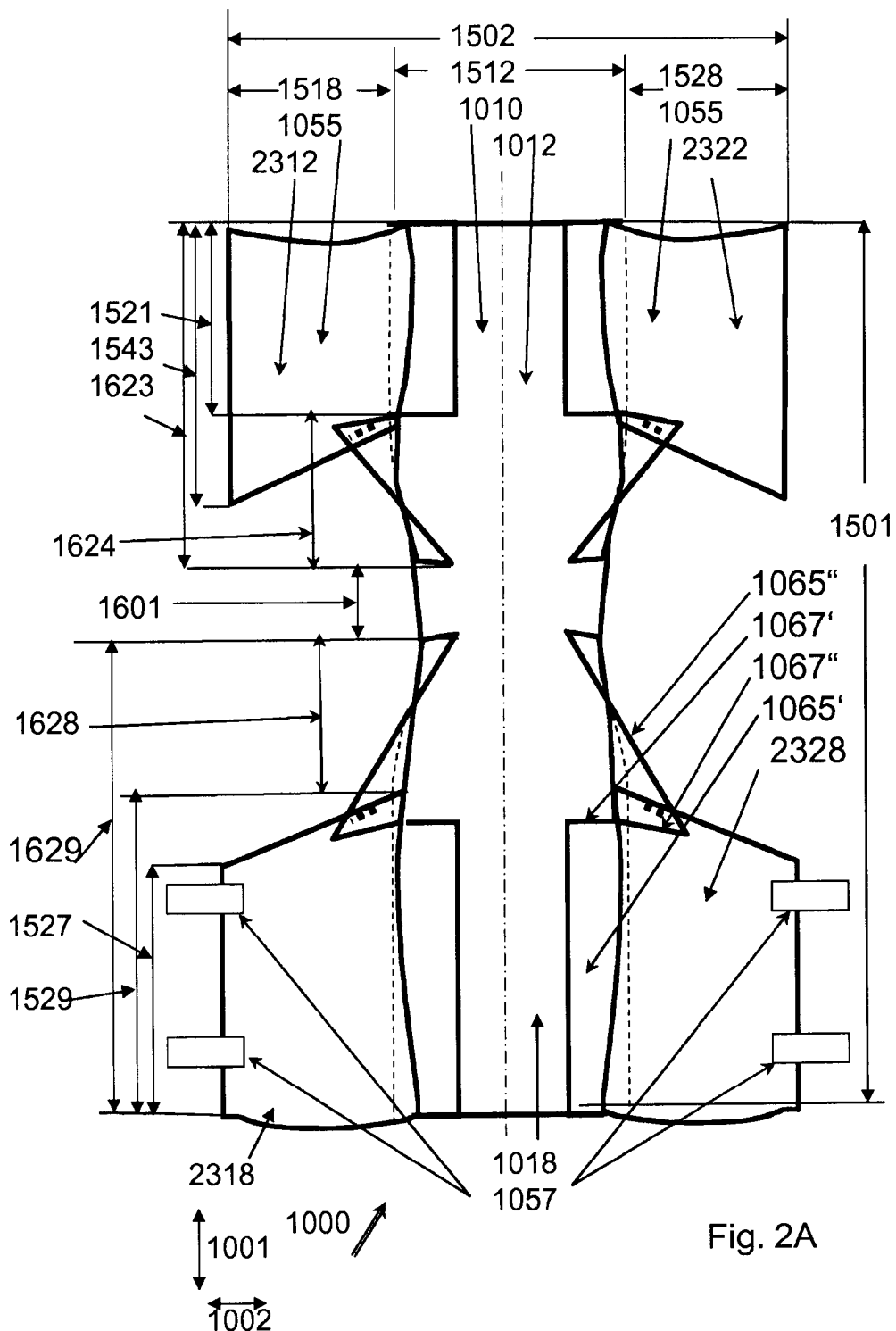
FIGS. 2 A and B depict schematically key dimensions of articles according to the present invention.
Figure 2D:
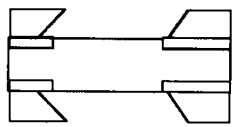
Figure 2G:
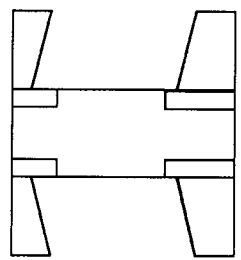
Figure 2C:
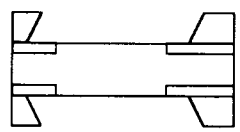
Figure 2F:
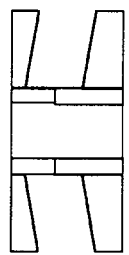
Figure 2E:
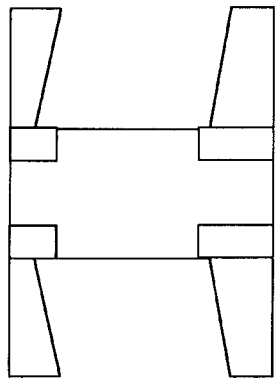
Figure 2B:
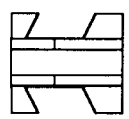

In the smallest size in FIG. 2B, the leg hoop gap 1601 is essentially zero, and the length of the centre piece 1010 is adapted thereto, thus providing the shortest overall product length and lowest rise of the product. The leg hoop circumference is determined by the length of the free portions of leg hoop materials 1624 and 1624 and the closure adjustment of the (front and rear) side panels. The rise of the product is low.

By merely enlarging the leg hoop gap (see FIG. 2C), the rise of the product increases. As the side panels are left at the length, the leg circumference increases. If also the cut length of the side panels (either front, or rear, or both) is increased, the leg circumference is reduced (see FIG. 2D). It should be noted that the length of the sidepanel along its connection line to the leg hoop is always shorter than the leg hoop.

When the leg hoop gap is essentially eliminated (as in FIG. 2B), but the width of the side panels and e.g., the width of the centre piece (see FIG. 2F) is/are increased, the rise, the waist circumference and the leg circumference may be varied.

The full flexibility is indicated in the context of FIGS. 2G and 2E, with increased side panel and centre piece width and leg hoop gap—whilst the total length of the leg hoop portions remains constant.

Thus it is a particular feature of the present design in its preferred execution, that a wide range of sizes can be covered based on defining one particular measure, namely the total leg hoop length, and adjusting easy-to-change parameters of other materials.

In a less preferred execution from a processing view, the leg hoop materials may be provided as discrete web pieces and may be spaced apart such that even shorter product options may be realized.

It should be noted, that the side panel width may be increased beyond the options as shown, e.g. when it is longitudinally folded, such as in a leporello fold. By this execution, the waist circumference may be increased even further.

It should be noted, that the leg hoop width can be varied as well. A narrower leg hoop width reduces the foreshortening of the x-directional centre piece side margins, a wider leg hoop width increases this effect. The leg hoop width must not be wider than the width of the inward overfold of the centre piece in the pre-use configuration.

Other limitations are more of practical nature, such that the dimensions of the centre piece (including the absorbent core) may be adapted according to the liquid handling requirements of the article. Further, the maximum leg hoop material length cannot exceed the pitch between two adjacent web handling sections.

Referring to FIGS. 3A and 3B, a suitable apparatus 5000 for the manufacturing of such an article is schematically depicted.

The equipment comprises supply means 5300, 5400, 5500 for providing the webs, at least two turrets 5100 and 5200 with various web handling means such as web support, combining, separation, or folding means, pusher means, such as for aiding discharging 5500, and control means 5800.

The supply means provide at least three webs, namely a side panel web, a leg hoop material web, and a centre piece web. Further supply means (not shown) may provide optional materials such as closure means like fastening tapes or secondary topsheets, which may also be already pre-combined with one of the three webs.

The sidepanel material web 5310 is provided from supply rolls 5320 having a preset roll width. Optionally, and often preferably, there may be more than one side panel roll (5320, 5320') for ensuring continuous web supply at roll changes by conventional "on the fly" splicing means. This may also allow "on the fly" change to a different roll width, according to varying sizes. Alternatively, a very short line stop for exchanging rolls may be acceptable.

In a preferred execution, the front and rear side panels of the article are coming from one and the same roll, though different materials are also within the scope of the present invention, such as when front or rear side panels are made from a non-elastic material, whilst the opposing rear or front side panels are made from elastic or extensible material. Sidepanels may also be pre-combined from different materials, such as when a narrow strip of elastic material is connected to a strip of non-elastic material, thus forming a multi-piece sidepanel. Preferably, the side panel is provided such that a web is completely or partly separated into two parallel strips, one each for the left and right side of the article. "Partly separated" refers to an execution, where the separation is incomplete, such as by an intermittent cutting line or a perforation line, such that the material remains connected during at least a part of the process, but is readily separated by lateral pull during the process, but preferably by the end user (sometimes also referred to as "perf 'n pop"). In an alternative execution, the "perf 'n pop" feature may be applied on the first turret.

The side panel may already be provided with closure means of any conventional type, such as adhesive or mechanical fastening tapes already applied thereto, or the closure means may be applied during the transfer to the first turret or on a turret.

The side panel material web is moved by a controllable web drive 5330 towards a separation means such as a cutting unit, here shown as a rotary knife/anvil unit 5340, though any other separation means is possible, and separated into side panel web pieces 5315 (length not shown to scale) having a predetermined length corresponding to the total length of the front and rear side panel in the article. The separation may be executed cross-directionally, angled, or curve-linearly. In a particularly preferred execution, the separation line may have a chevron-type shape.

The length of a side panel piece or pieces is the sum of the length of the front and rear side panel in the article, which not necessarily need to be the same. Like the side panel material, the leg hoop material web 5410 may be provided by the leg hoop material supply means 5400 as a single web, which may be completely or partially separated, or as two parallel webs, which may be unwound from one roll 5420 and or from two rolls. The leg hoop web material is moved by a controllable drive 5430.

The centre piece web 5510 is provided by the centre piece supply means 5500. In case of manufacturing absorbent articles, the centre piece typically comprises liquid absorbent material 1035, a liquid impervious backsheet 1045, and a topsheet 1025. Optionally, the centre piece may comprise further elements, such as—without any limitation—secondary topsheet, or elastic elements. The centre piece web may be unwound from a supply roll 5520, spool, or fed from a box ("festooned"). The centre piece web may also be provided "on-line", such as from conventional core former (not shown). The absorbent element 1035 of the centre piece may be rectangular or have a length—width shape and/or a thickness-directional profile. The absorbent element may be enveloped between a backsheet and a topsheet in any conventional manner. In case that there is no particular absorbency requirement for the article, such as may be the case for disposable underwear, the absorbent element may be omitted, or the centre piece may only be a single web material. Within the essentially continuous centre piece web, repeating centre piece segments 5515 correspond to an article. The repeating segments are separated from each other by a centre piece segment demarcation line, which may be visible or noticeable, or which may appear as an abstract "thought" line. In a preferred execution, the centre piece web is longitudinally folded along two parallel foldlines, such that its side margins are positioned side by side along a line parallel to the centre piece web centre line, preferably in close proximity to the centre piece web centre line. In all embodiments, the backsheet forms the outer layer of the longitudinal side sections of the centre piece just prior to its combining to the combined leg hoop/side panel piece. This is achieved either by laying down the backsheet as upper layer on turret 5200, or by overfolding a centre piece web with the backsheet as lower layer on turret 5200.

Each of the first 5100 and the second turret 5200 comprises at least two web handling or treatment sections, which are essentially identically designed. These may comprise web support means (5121, 5122, 5123, 5222, 5228, 5232, 5238), such as described in detail in WO06/103487.

Such a web handling means is connected to the frame of the turret or turret section. The web handling means may be connected moveably relative to the frame of the turret segment respectively to other web handling means, but preferably—in particular for the first turret—they are connected in a fixed relative position to the frame. A web handling means comprises a surface, which is moveable relative to the frame. The surfaces are adapted to temporarily receive and release a web and thus may have fixation means to keep at least portions of the web affixed to portions of the web support, such as by using vacuum belts or drums. One of the surfaces of one or more of the web support means may coincide with the surface of the turret.

In a particular execution, the web support means is a belt system with a variable speed drive system, such as well known servo drives, which enable to move the belt forward or rearward, relative to the frame of the turret. In a preferred execution, the belt or a chain type surface can be moved virtually endlessly, without being restricted by the machine frame.

A first turret 5100 is used to combine spaced apart side panel pieces 5315 to the leg hoop web material 5410, which, however, may already be partially or completely separated, whereby the pieces may be but are preferably not spaced apart.

The turret is arranged such that along the direction of rotation of the turret the side panel web may be positioned first onto the surface of the turret and the leg hoop material web onto the side panel web pieces.

The first turret may comprise at least two, as shown in FIG. 3 three, optionally more turret segments 5110, 5111, 5112 each comprising at least one web support means 5120, 5121, 5122. The circumference of the turret divided by the number of turret segments determines the pitch of the turret. The web support means may comprise controllable web attachment means. In a preferred execution, these may be executed as having a rounded or multi-edge surface so as to cover almost the total surface of the segments and hence of the turret 5100 and the cut pieces 5315 of the side panel web may be positioned preferably at matching speed thereon and temporarily affixed thereto. During transfer of a sidepanel piece—which may be of different length for different product sizes—the web support means surface speed may be adjusted by controllable drives of the web support means, to match the speed of the incoming piece. When their transfer is completed, two subsequent pieces may be spaced apart from each other by controllable drives of the web support means, e.g. when accelerating the web support surface speed relative to the constantspeed of the side panel knife drive. In a simplified, less preferred execution, the first turret 5100 may act as anvil roll working against the knife roll of separation unit 5340. In a particular execution, a conventional vacuum roll may be adapted to function as an anvil for a counteracting rotating knife.

After the leg hoop material web 5410 is positioned onto the spaced apart side panel web pieces 5315 such that the leg hoop material is—in the preferred execution—continuous and subsequent side panel pieces are spaced apart from each other, the two materials may be combined by a combining means 5130 to form the leg hoop/side panel composite 5190. In a preferred execution, this is done by using a flexible anvil ultrasonic bonding unit, such as described in more detail in co-pending application GB 2484369. Preferably, the connecting is phased such that it is applied only to the regions of overlying materials, though depending on the robustness of the process and the properties of the webs, the connecting-/bonding line may be uninterrupted/continuous. In a less preferred execution, where the leg hoop material is delivered shorter than the pitch of the first turret, the leg hoop overlaying a sidepanel will be moved together with the sidepanel to the right position for connecting the two discrete pieces.

The first turret further comprises a separating means, here shown as a rotary knife 5140 which cooperates with anvils 5145 for separating subsequent pieces of the leg hoop/sidepanel composite web. Preferably, the separated leg hoop web pieces remain essentially adjacent to each other, i.e. are not intentionally spaced apart from each other. Further, predominantly cross-directionally extending separation lines 1067 may be applied to the leg hoop web prior to or whilst being transferred to the first turret 5100, such as in a conventional rotating knife and anvil unit 5440. Optionally, at the infeed to the first turret there may be a further machine direction separation unit 5160 for completely or partially longitudinally separating the leg hoop web. Alternatively, longitudinal separation of the composite leg hoop/sidepanel web is done on the first turret by slitting unit 5160'.

Optionally, a combining glue unit 5150 may apply an adhesive to the surface of the composite—in an alternative the combining glue may be applied to the backsheet side of the centre piece on the second turret (see below).

As the web support means comprises a controllable web attachment means, such as a controllable vacuum unit, the webs may be readily transferred from the first turret 5100 to the second turret 5200.

The second turret 5200 is arranged to receive the side panel/leg hoop composite 5190 from the first turret 5100, after the centre piece web 5510, which is delivered by centre piece supply unit as described in the above, is positioned—longitudinally folded or unfolded—on the turret surface.

The turret comprises at least two, preferably and as shown in FIG. 3 six, but possibly more essentially identically designed turret segments 5210. The turret segments comprise web handling means, at least two, more preferably, as shown in the particular execution of FIG. 3, four thereof, with two thereof being positioned such that one of the preferably three web support surfaces forms the surface of the turret, a leading (5222) and a trailing (5228) outer web support. Two further web support means may be positioned radially inwardly from the outer ones, namely a leading (5232) and a trailing (5238) inner web support.

Preferably, the web support means have a triangular configuration, such that the outer web support means each have an outer surface corresponding to the turret surface, and a first gap surface facing the first gap 5441 between the two outer web support means 5222 and 5228. The third surface of the leading outer web support means 5222 faces a first surface of the leading inner web support means 5232 such that a second gap 5442 is formed, and the third surface of the trailing outer web support means 5228 faces a first surface of the trailing inner web support means 5238 such that a third gap 5443 is formed. The second surfaces of the leading and trailing inner web support means are facing each other thusly forming a fourth gap 5444. In the particular arrangement as shown in FIGS. 3A and B, the four gaps may be in a cross-like arrangement.

Each segment of the turret may further comprise a pusher means 5550, adapted to move radially in- and outwardly in the fourth and first gap.

Optionally, the web support means may be adapted to be moveable relative to the turret segment such as to adjust the widths of the gaps, preferably at least the first and fourth gap.

The turret may further comprise elements for adding and/or engaging closure means to the article and/or closing the article to a pants-style product (not shown in FIG. 3).

In a first execution, the side edges, which are positioned outwardly (i.e. away from the center piece) in a ready-to use or in-use configuration of a front and a rear side panel, may be connected to each other, preferably by an ultrasonic welding apparatus, such as described in the copending patent application GB 2484369.

Alternatively, closure tapes may be fed and attached to the side panels already before the side panel web is fed to the first turret, or at any later stage on the first turret. These closure tapes may be "conventionally" configured, i.e. like in current open diaper style products, such that the user will lift a portion of the closure tabs, which are typically connected to the rear side panels.

In yet a further alternative, one tab of a closure tape is permanently connected to a side panel, often to a rear one during use, but alternatively and for certain designs preferably to a front one during use. The opposite tab is removeably connected to the respectively opposite front or rear side panel, such that a closed pants-style structure results, which can be easily donned, removed, or size adjusted.

The side panel connecting tool as well as the tape applicator can be shut on and off, such that if a turret comprises both of these equipments, it may change from closed pant style products to open-style or open-style pre-closed articles without an interruption ("on the fly").

In a preferred embodiment, there is both a tape applicator and a side-seamer, whereby one of these elements is positioned so as to act on the article in the second or third gap, and one in the fourth gap.

There may be one of each of these elements in each segment, or there may be one of these elements for the turret, whereby the articles of the segments are treated consecutively when passing by.

The turret further comprises separating means 5570 for separating individual web pieces from the continuous centre piece web so as to form individual pieces which may already be combined with the side panel/leg hoop composite 5190. The separating means may be a rotary knife 5570 cooperating with anvils 5575 as being part of the turret segments. Optionally, in addition or alternatively to a combining glue applicator of the first turret, the second turret may comprise a glue applicator (not shown).

The treated articles may be stacked after or whilst they are removed from the turret by a stacking means 5600. Preferably this is achieved by a helical screw, such as described in the above referred patent application WO06/103487, cooperating with the pusher bar 5550.

The equipment further comprises a data processing and control unit 5800, which adapts the settings for the various speeds of the webs, turrets, web support means etc. according to parameters, which may be preset according to the desired size of the article. Upon a size change, these parameter can be reset, and the size change can occur "on the fly" by merely adjusting the various speeds, optionally also by changing the supplied webs, which also can take place "on the fly".

Having thusly described the equipment according to one aspect of the present invention, the process steps for executing the manufacturing process according to another aspect of the present invention are now described in more detail by referring to the set up as described in the context of FIG. 3. Additionally, in FIG. 4 A to E, the web support means of a segment of the second turret is shown for various stages of a final composite 5519 formed by the leg hoop/side panel composite 5190 and the centre piece, being moved through the various gaps. Therein, the arrows respectively the lack thereof denote the movement direction respectively the lack thereof of the respective web support means.

Thus the method comprises the following steps:
Providing a first essentially continuous web 5510 for forming the centre piece at a predetermined first/centre piece web supply speed. Like any speed variations in the context of the present invention, they can preferably be varied continuously over their full control range.
The continuous web comprises—visible or hypothetical—demarcation lines between subsequent segments 5515 of the centre piece which will be part of subsequent articles, thereby defining a leading and a trailing part of the centre piece and a centre piece segment machine direction extension, which corresponds to the length direction of the article. In the case of absorbent articles, the centre piece may comprise an absorbent core 1035, which may be rectangularly or irregularly shaped, and which may be of uniform thickness or exhibiting a thickness profile. The absorbent core may be enveloped between a backsheet 1045, which is intended to be positioned away from a wearer during the intended use, and a topsheet 1025 on the opposite surface.
The centre piece may be formed of any conventional materials suitable for the intended use. The centre piece may be formed "in-line" such as by a conventional core forming process step and a subsequent enveloping between topsheet and backsheet. The centre piece may be formed "off-line" and may be delivered on rolls, spools, or other suitable means, such as in boxes ("festooning").

The centre piece segment length 5515 may be essentially the same for different sizes, or may be different for different sizes.

The change between different centre-piece lengths may be done "on the fly", such as when the centre piece is made of absorbent cores as may be cut from a continuous roll at a cut length varying by product size, and enveloped between topsheet and backsheet at a varying cut length. The change may also be executed by having a continuous splice between roll, spools or boxes with different centre piece or absorbent core lengths.

The centre piece width may be the same for different sizes, but may also vary such as by using different rolls with "on the fly splicing".

Providing a second essentially continuous web material 5410 for forming the leg hoop material strips at a predetermined variable second web or leg hoop material supply speed.

This material may be provided from two separate rolls, each having a roll width corresponding to the height of the leg hoop during use. Alternatively, the material may be provided on one roll having a width corresponding to the double of the height of the leg hoop during use, and both the material for the left and the right leg hoop. In a preferred execution, the splitting of the web is done online, although it may already be pre-split on the roll. The separation may be a complete separation, or a partial one, such as by intermittent cuts or perforations. In a preferred execution, the leg hoops are completely separated in machine direction and are partly separated in cross direction e.g., by a knife assembly 5160. A separation unit 5440 can apply four predominantly cross-directionally extending separation lines, such as slits, to the leg hoop web prior to or whilst being transferred to the first turret 5100. Each two slits may be mirror symmetrical to the centre line and can run into each other. Each a pair of such symmetrical slits is at a location, which, after the side panel pieces are added, are adjacent to the longitudinal front and rear edges of the side panel pieces.

The roll width may be the same across the desired size range, or it may be varying such as doing a size change by splicing in a different width material.

Providing a third essentially continuous web 5310 for forming side panels at a predetermined variable third web or side panel supply speed.

The product under consideration comprises four side panels (front/back and left/right), which in a particular embodiment may be made all of the same material, which may further be supplied on a single roll.

It is, however, contemplated, that the front and rear side panel materials are different, such as when one thereof is elastic or extensible, and the other one not. In this instance, the two materials will be provided separately and positioned (as described herein below) machine-directionally adjacently to each other.

Providing a first turret 5100 as described in the above for combining the second (leg hoop, 5410) and third (side panel, 5310) web materials, the turret being mounted for rotating at a predetermined variable first turret speed and comprising the following:

at least two, in a preferred execution three, but possibly also more web support means 5120, each comprising a web support means surface which can be moveable at a predetermined variable web support means surface speed, relative to the turret surface speed and being adapted for temporarily attaching the first or side panel web and second or leg hoop web material or segments thereof thereon;

a side panel separating means 5340 for separating pieces at a predetermined variable cut length from the continuous web. The separation means may be integral with the turret or—in a preferred execution—separate;

a hoop/side panel composite separating means 5140 for separating pieces of the side panel/leg hoop composite at a predetermined cut length from the continuous web, which may be integrated with the turret or separate;

Providing a second turret 5200 for combining the side panel/leg hoop composite 5190 with the centre piece web 5510, preferably positioned in a "kissing relation" to the first turret 5100. The second turret 5200 comprises:

at least two web handling sections 5210, each web handling section comprising at least two, preferably three, more preferably four web handlings means (5222, 5228, 5232, 5328) which form a first (5441), second (5442), third (5443) and fourth (5444) gap between them as described in the above, all of which comprise a web support means surface which is moveable at a predetermined variable web support means surface speed, relative to the turret surface speed;

a centre piece separation means 5570 for separating the assembled pieces at a predetermined variable cut length from the continuous web which may cooperate with anvils 5575;

an article discharge means 5600;

optionally means for permanently connecting front and rear parts of the article, means for applying openable closure means, and further optionally means for closing the article by releasably connecting front and rear parts of the article with the openable closure means (not shown);

optionally glue application means adapted to apply adhesive to the total or parts of the surface of the web (not shown).

Providing a controlling unit 5800 for adjusting respective speeds and positioning of web support means, connecting means, applications means or the pusher means.

Feeding the side panel web 5310 towards the side panel separating means 5340 at a first web speed and separating a side panel piece 5315 from the side panel web at a side panel cut length adapted to the specific dimensions of the predetermined article size.

Positioning the side panel piece 5315 on one of the first turret web support means, thereby spacing subsequent side panel pieces apart by adjustment of first turret web support means surface speed.

Feeding the leg hoop web 5410 to the web support means of the first turret at a predetermined variable speed such that it overlays the side panel piece 5315 whilst being preferably a continuous web or in case of being pre-cut into subsequent pieces, these being preferably unspaced from each other. However, and less preferred for processing reasons, the leg hoop pieces may be cut shorter than the pitch of the first turret. As indicated in FIG. 5A showing schematically the top view of the first combining unit 5100, the leg hoop material 5410 (here shown partially lifted up) may be fed such that it essentially overlays the longitudinal centre and the side panel pieces 5315 (here also shown partially lifted up) project laterally outwardly, i.e. away from the centre line. In the execution shown, an ultrasonic horn may then cooperate with anvils, here shown as a flexible anvil, as described in the above referenced application GB 2484369. In an alternative arrangement as shown in FIG. 5B, the leg hoop material 5140 is positioned laterally more outwardly. Consequently, also the anvils are positioned more outwardly, and two sonotrodes 5130' and 5130" may be used for connecting the leg hoop material to the side panel pieces 5315, which now project to or even over the longitudinal centre line.

Connecting the side panel piece 5315 and the leg hoop web 5410, preferably by ultrasonic welding 5130 along a curved connecting line and adjacently of the cross-directional slits in the leg hoop material of the previously described step to form the side panel/leg hoop composite 5190.

Optionally applying combining adhesive 5150 onto the surface or a portion of the surface, such as the leg hoop material of the side panel/leg hoop composite 5190.

Separating subsequent pieces of the side panel/leg hoop composite 5190 in the spacing between two subsequent side panel cut pieces 5315 at a predetermined/variable leg hoop material cut length.

Feeding the centre piece web 5510 at a predetermined variable speed to the second turret such that the backsheet 1045 is positioned towards the second turret surface. Either already before feeding or whilst feeding, the left and right centre piece side margins are longitudinally overfolded, such that the topsheet surfaces are facing each other in these overfolding zones. Optionally, the centre piece web is not folded longitudinally, in which case the backsheet side of the centre piece is away from turret 5200. Optionally, a tack down connection may be applied, such as by ultrasonic bond, or an adhesive application such that the overfold remains also in the in-use configuration. Optionally, the combining adhesive may be applied to the centre piece 5510 web or portions thereof instead of or in addition to the application to the combined side panel/leg hoop composite 5190.

Adjusting the surface speed of the two outer web support means 5222 and 5228 of the second turret such that a predetermined portion in the crotch region of the centre piece web is dislocated radially inwardly into the first gap 5441, thereby forming a cross-directional fold. Upon further rotation of the turret 5200, more of the crotch section of the centre piece may be folded radially inwardly, whereby the leading portion remains essentially stationary on the leading outer web support 5222, until the length of the non-dislocated portion of the centre piece on the surface of the second turret is adapted in its length to the pitch of the first turret, in a preferred execution to the length of the discrete pieces of the combined leg hoop and side panel composite (see FIG. 4A).

Rotating the first and the second turret at a matched surface speed such that the combined leg hoop and side panel composite pieces 5190 are positioned in registry with the portions of the centre piece web 5515, which are not dislocated radially inwardly into the first gap 5441 (see FIG. 4B). The separation line 5195 between two subsequent leg hoop/side panel composites should be positioned in registry with the first gap 5441. By the effect of the previously applied adhesive, the pieces are connected to each other, thusly forming an essentially continuous web of essentially finished articles.

Separating individual finished articles 5519 from the essentially continuous web of essentially finished articles.

Transferring the cut article 5519 either further into gap 5441, thereby completing the cross folding, and with the waist edges leading into a stacking device 5600, or alternatively transferring the cut article 5519 out of the first gap 5441 into gap 5443 and subsequently into gap 5442 by appropriately adjusting the web support means speeds and directions, thereby unfolding the cross fold while moving the article towards the backside of support belt 5228 and 5222 (see FIG. 4C).

In one alternative execution, the article 5519 can be transferred out of the second gap by appropriately adjusting the web support means speed, such that either both the front and rear part of the article are moved into the fourth gap 5444, such that the pusher bar 5550 is located between these or such that the pusher bar can be inserted there between (not shown in FIG. 4), or either the front or rear part of the article is moved into the fourth gap, such that the pusher bar is or can be located to contact the topsheet surface of the article, and the respective other part is moved into the third gap transferring the article into gap 5441 by means of pusher 5550.

However, in another alternative execution as indicated in FIG. 4, in case the article is longitudinally folded, it can be transferred out of the first gap directly into the second and third gap with its leading and trailing ends, and its positioning can be adjusted such that the mid portion of the article is in registry with the pusher bar, which upon activation cooperatively with appropriately moving web supports means, moves the article with its backsheet surface first through the first gap.

Optionally connecting front and rear portions of the article at the unconnected longitudinal side margins of the side panels to form a closed pants-style article.

Optionally applying closure means to the front or rear portion of the article, optionally further connecting the front and rear portions of the article by means of these closure means so as to form re-openable pants-style articles.

Transferring the article by appropriately adjusting the web support speeds and optionally supported by radial movement of the pusher bar through the first gap 5441, with the cross-directional fold leading, out of the turret.

Further handling the article, such as by packing, preferably by receiving the article in a helical screw, such as described in WO06/103487.

The skilled person will readily realize that all speeds can be adjusted by a processing and control unit 5800. Also, it should be noted, that the above order of the description of the processing steps does not necessarily imply that all steps have to be executed in this order, but that certain steps can be—and preferably are—executed simultaneously, or even earlier than steps described before.

In a first control modus, all speeds may be adjusted proportionally to one reference variable, such as the centre piece web supply speed, such that the number of produced articles per time unit can be set.

In a second control modus, the various speeds can be adjusted relative to each other so as to create varying size articles.

As described in the above for the preferred execution, the various sizes can be defined relative to a basic dimension, such as the total cut length of the leg hoop material strip.

All changes of the product overall length, or the length of the side panels can be readily adjusted "on the fly". Even width changes of supplied materials can be automatically made by using automated splicer units. The flexible ultrasonic bonding unit can cope with changing side panel dimensions by appropriately adjusting the leg hoop to side panel bond curvature. In a less preferred execution, also the length of the separated leg hoop material may be varied.

Even further, in case of having both closure means applicators and side seamers as equipment, also closed pants-style products, open diapers, or pre-closed, re-openable diapers can be produced on the same line with an "on the fly" change possibility. As all of these speed changes can be done simultaneously and without stopping of the machine, let alone changing parts of the machine, the present invention allows producing varying sizes "on the fly".

It should be noted, that the above explanation of the various aspects of the invention does not cover all executional variants, but that the various equipment details of processing steps may also be equivalently functioning ones.

Thus, one or both of the turrets may be replaced by other web path splitting means with repeating web handling or treatment sections, as described in more detail in WO06/103487.

As described, it is a preferred execution, that the first and the second turret are positioned in a "kissing relation", such that the leg hoop/side panel composite of the first turret may be directly transferred onto the centre piece on the second turret. However, if the effect of combining the leg hoop/side panel composite and the centre piece web is achieved by other means, such as by additional web support means, it should be considered as an equivalent execution and also within the scope of the present invention.

The separating of the various webs can be performed by any conventional separation method.

Instead of using various web support means, the foreshortening of the centre piece web may be achieved by rolling the middle or crotch portion such as described in more detail in co-pending application WO2011/086054A1. In this case, the discharge of the product may be further modified by rolling up the article completely.

FIG. 6 shows a further execution of the present invention, wherein the connecting of the side panel material 1055 and the leg hoop material 1065 is executed whilst the overlap of the two materials is extended, as can be achieved by opening the separated edges of the leg hoop material from each other essentially along the direction of the longitudinal side margin. Thus, FIG. 6A shows a view of an article as in FIG. 1B, i.e. in its pre-use configuration, here shown with non-rectangularly cut side panels 1055. Also, closure means, such as adhesive or mechanical fastener tapes are shown connected to front or rear side panels. In FIG. 6B an enlarged view shows side panel 1055 overlying the leg hoop web 1065 in a flat configuration, with indications of the connecting line 1069 between the two materials and the separation line 1067 in the leg hoop web. FIG. 6C shows schematically that the separation line is opened and a gap is formed between the separation line edges 1067' and 1067" such that the leg hoop web is almost or even completely separated into a first (1065') and a second (1065") portion. This gap can be achieved by lifting the respective portion of the leg hoop material away from the base level of the opposite side margin, or by rotating one or both of the edges away from each other. When the connecting to the side panel web is executed whilst the gap is open, the longitudinal side margin of the combined leg hoop and side panel webs will exhibit a greater length than the opposite side margin—in FIG. 6B indicated by the wavy side margin of the leg hoop material 1055. The effect in the product is indicated in FIG. 2A, showing the top view of an article in a ready-to-use configuration. As shown the leg hoop web comprises first portion 1065' and a second portion 1065", separated by the separation line edges 1067' and 1067" respectively. The first portion 1065' is connected to the centre piece 1010. The second portion 1065" is connected by connecting line 1069 near the separation line 1067" to the side panel 1055 and at least with its opposite cross-directionally extending edge to the centre piece. As the leg hoop is connected along the longitudinal side margin of the centre piece thereto, the second portion of the leg hoop web will twist upon opening of the side panel when transferring the article from its pre-use configuration to its ready-to-use configuration. Whilst this also applies to executions without spacing apart the separation edges 1067' and 1067", in the execution with the increased gap the portion of the leg hoop, which is positioned downwardly on the upper thigh during use (i.e. which is further away from the crotch region) is of greater length, thereby providing more uniform tensioning around the leg, and a snug fit.

The invention claimed is:

1. A method for the manufacture of an article,
said article comprising
segments of a centre piece web material, separated pieces of a side panel web material, and pieces of a leg hoop web material connected to said side panel web pieces,
said method comprising the steps of
providing a first essentially continuous web for forming the centre piece at a predetermined variable first web supply speed;
providing a second essentially continuous web material for forming the leg hoop materials at a predetermined variable second web supply speed;
providing a third essentially continuous web material for forming side panels at a predetermined variable third web supply speed;
providing a first turret for combining the second and third web materials, the turret being mounted for rotating at a predetermined variable first turret speed and comprising
at least two web support means, each comprising a web support means surface which can be moveable at a predetermined variable web support means surface speed, relative to the turret surface speed and being adapted for temporarily attaching the first and second web material or segments thereof thereon;
a side panel separating means for separating pieces at a predetermined variable cut length from the third web;
a leg hoop material or side panel/leg hoop composite separating means for separating pieces of the side panel/leg hoop composite at a predetermined cut length;
providing a second turret for combining the side panel/leg hoop composite with the centre piece web, preferably positioned in a "kissing relation" to the first turret and comprising
at least two web handling sections, each web handling section comprising at least two, preferably three, more preferably four web handlings means each comprising a web support means surface which is moveable at a predetermined variable web support means surface speed, relative to the turret surface speed,
a centre piece separation means, and
an article discharge means;

providing a controlling unit for adjusting respective speeds and positioning of web support means, connecting means, applications means or the pusher means;

feeding said side panel web towards said side panel separating means at a first web speed and separating a side panel piece from the side panel web at a side panel cut length;

positioning the side panel piece on one of the first turret web support means, and spacing subsequent side panel pieces apart by adjustment of first turret web support means surface speed;

feeding the continuous leg hoop web or separated pieces thereof to the web support means of the first turret at a predetermined variable speed such that it overlays the side panel piece;

connecting the side panel piece and the leg hoop web, preferably by ultrasonic welding to form the side panel/leg hoop composite;

separating subsequent pieces of the side panel and leg hoop material in the spacing between two subsequent side panel cut pieces at a predetermined variable leg hoop material cut length if the leg hoop material has been fed to said first turret as a continuous web;

feeding the centre piece web at a predetermined variable speed to the second turret;

applying combining adhesive onto the surface of the side panel/leg hoop composite or to the centre piece;

adjusting the surface speed of the two outer web support means and of the second turret such that a predetermined portion in the crotch region of the centre piece web is dislocated radially inwardly into the first gap between two web support means;

rotating the first and the second turret at a matched surface speed such that the combined side panel/leg hoop composite pieces are positioned in registry with the portions of the centre piece web, which are not dislocated radially;

separating pieces of said centre piece web, optionally after the combination with said side panel/leg hoop composite to form individual articles;

transferring the article out of the turret.

2. The method according to claim 1, further comprising one or more of the steps of applying a curved connection when combining said side panel web and said leg hoop web;

applying ultrasonic energy, preferably working against a flexible anvil for connecting;

further treating the individual article 5519 in said treatment section or on said turret;

connecting permanently front and rear portions of the article at the unconnected longitudinal side margins of the side panels to form a closed pants-style article;

applying closure means to the front or rear portion of the article;

connecting the front and rear portions of the article by means of these closure means so as to form re-openable pants-style articles;

maintaining said treatment sections and web handling means on said turret in a fixed position relative to each other;

overfolding the longitudinal side margins of said centre piece web prior to or during feeding said centre piece web to said first turret;

applying predominantly cross-directionally extending connecting lines to said side panel pieces and said leg hoop material whilst the first longitudinally extending side margins of the overlaid side panel and leg hoop webs are extended compared to the second opposite longitudinally extending side margin of the leg hoop web, which is the one which is closest to the crotch crease on the product in use.

3. The method of claim 1 for an on the fly size change in the manufacture of at least two sizes or types of article series, said article comprising segments of a centre piece web, which exhibit different dimensions for different sizes at least for the length of the article corresponding to the machine direction of the manufacturing method, separated pieces of a side panel web, which exhibit different dimensions for different sizes at least for the length of the article corresponding to the machine direction of the manufacturing method, and completely or partially separated pieces of a leg hoop web, which exhibit essentially the same dimension for the varying sizes, said method further comprising the steps of:

selecting one or more characteristic design parameter for the article sizes or types, adjusting the variables of the process steps according to a preset correlation as being stored or calculated in a programming and control unit.

\* \* \* \* \*

UNITED STATES PATENT AND TRADEMARK OFFICE
CERTIFICATE OF CORRECTION

| | | |
|---|---|---|
| PATENT NO. | : 9,248,055 B2 | Page 1 of 1 |
| APPLICATION NO. | : 14/348429 | |
| DATED | : February 2, 2016 | |
| INVENTOR(S) | : Christoph Schmitz | |

It is certified that error appears in the above-identified patent and that said Letters Patent is hereby corrected as shown below:

In the claims,

Column 24, Line 3, Claim 2:

After "further treating the individual article"
Delete "5519".

Signed and Sealed this
Twelfth Day of April, 2016

Michelle K. Lee
*Director of the United States Patent and Trademark Office*